United States Patent
Wen et al.

(10) Patent No.: US 9,939,392 B2
(45) Date of Patent: Apr. 10, 2018

(54) DEMODULATION OF INTENSITY MODULATION IN X-RAY IMAGING

(71) Applicant: The United States of America, as Represented by the Secretary, Department of Health and Human Services, Washington, DC (US)

(72) Inventors: Han Wen, Bethesda, MD (US); Houxun Miao, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 197 days.

(21) Appl. No.: 15/021,675

(22) PCT Filed: Sep. 11, 2014

(86) PCT No.: PCT/US2014/055224
§ 371 (c)(1),
(2) Date: Mar. 11, 2016

(87) PCT Pub. No.: WO2015/038793
PCT Pub. Date: Mar. 19, 2015

(65) Prior Publication Data
US 2016/0231258 A1 Aug. 11, 2016

Related U.S. Application Data

(60) Provisional application No. 61/877,219, filed on Sep. 12, 2013.

(51) Int. Cl.
*G01N 23/04* (2006.01)

(52) U.S. Cl.
CPC .................................. *G01N 23/04* (2013.01)

(58) Field of Classification Search
CPC ...................................................... G01N 23/04
See application file for complete search history.

(56) References Cited

U.S. PATENT DOCUMENTS

| | | |
|---|---|---|
| 2013/0028378 A1 | 1/2013 | Stutman et al. |
| 2013/0208861 A1 | 8/2013 | Handa |
| 2014/0056407 A1 | 2/2014 | Goldammer et al. |

FOREIGN PATENT DOCUMENTS

| | | |
|---|---|---|
| DE | 10-2011-006662 | 10/2012 |
| EP | 2746754 | 6/2014 |

OTHER PUBLICATIONS

International Search Report and Written Opinion from International Application No. PCT/US2014/055224, dated Feb. 19, 2015, 9 pages.

*Primary Examiner* — Mark R Gaworecki
(74) *Attorney, Agent, or Firm* — Klarquist Sparkman, LLP

(57) ABSTRACT

X-ray grating based and grid based imagers formed a fringe pattern modulated by a specimen. An X-ray beam is scanned so that the fringe pattern is modulated by these specimen along a plurality of projection directions. Corresponding fringe patterns are detected and aligned so as to produce a specimen phase image. X-ray beam scanning is based on electric or magnetic deflection of an electron beam to an X-ray generating target.

28 Claims, 10 Drawing Sheets

SPATIAL COORDINATE

FIG. 10A  FIG. 10B
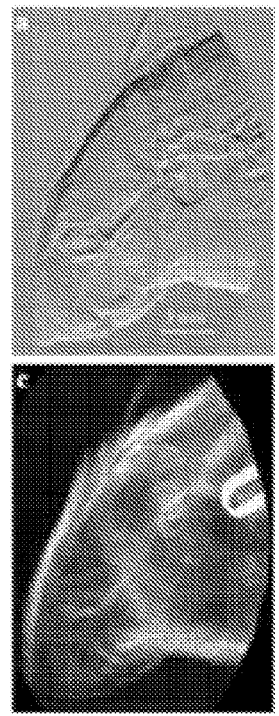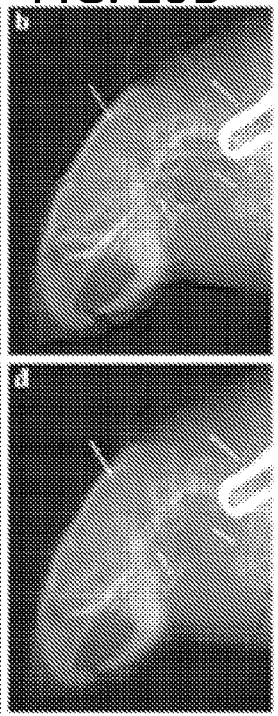
FIG. 10C  FIG. 10D
FIG. 11A  FIG. 11B
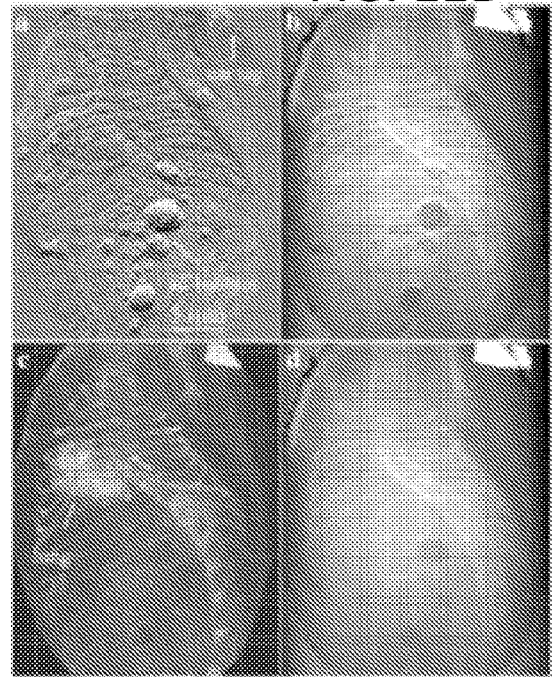
FIG. 11C  FIG. 11D

DEMODULATION OF INTENSITY MODULATION IN X-RAY IMAGING

CROSS REFERENCE TO RELATED APPLICATIONS

This is the U.S. National Stage of International Application No. PCT/US2014/055224, filed Sep. 11, 2014, which was published in English under PCT Article 21(2), which in turn claims the benefit of U.S. Provisional Application No. 61/877,219, filed Sep. 12, 2013. The provisional application is incorporated herein in its entirety.

ACKNOWLEDGMENT OF GOVERNMENT SUPPORT

This invention was made by an agency of the United States Government or under a contract with an agency of the United States Government. The name of the U.S. Government agency is: the Department of Health and Human Services, National Institutes of Health.

FIELD

The disclosure pertains to image formation in phase-grating based X-ray imaging.

BACKGROUND

Conventional X-ray imaging provides image contrast based on absorption and often provides low contrast for biological specimens. Phase contrast X-ray imaging can provide superior contrast, diffraction enhanced images have been obtained using Bragg analyzer crystals and free space propagation of transversely coherent waves. X-ray differential phase contrast (DPC) imaging using a Talbot grating interferometer has been demonstrated. Quantitative phase retrieval by a phase stepping method has also been demonstrated. Unfortunately, phase stepping is a mechanical process in which one grating is physically moved in multiple steps over a grating period in order to obtain a single differential phase image. Accurate mechanical movement of centimeter-size objects such as X-ray gratings at a sub-micron level is inherently slow, and difficult to reproduce precisely without a static and stabilized platform. In common configurations including fluoroscopes and CT scanners, precision motors must be mounted on moving gantries, leading to additional mechanical instability. X-ray phase imaging methods and apparatus that do not require difficult to realize mechanical movements are needed.

Scattering of X-rays by the material of a specimen creates a diffuse background in the images which degrades the quality of radiography and CT images. Absorption grids are placed in the beam to either physically block the scattered X-rays, or provide a scatter-corrected image based on demodulating the projected grid pattern in the image. In this case, the grids must be mechanically moved in order to remove the grid pattern in the final images. This mechanical movement is inherently slow, and mechanical actuators add cost and require maintenance. Methods that do not require mechanical movements also benefit these applications.

SUMMARY

In some example, apparatus comprise an X-ray source configured to produce a scannable X-ray beam. A plurality of diffraction gratings or absorption grids is situated to receive the scannable X-ray beam, direct at least a portion of the scannable X-ray beam to a specimen, and produce X-ray fringes modulated by the specimen. A scan controller is coupled to scan the scannable X-ray beam to a plurality of positions and produce a corresponding plurality of X-ray fringe patterns. An X-ray detector is situated to receive the X-ray fringe patterns and produce associated electronic images. An image processor is configured to align the electronic images associated with the X-ray fringe patterns and produce a specimen image based on the aligned electronic images. In some examples, the X-ray source includes an electron beam source that is directed to a target so as to produce the scannable X-ray beam, and a coil coupled to scan the scannable X-ray beam based on a current applied to the coil. In other representative examples, the image processor is configured to produce the specimen image based on the aligned electronic images of the specimen and aligned electronic images associated with a set of reference X-ray fringe patterns. In some embodiments, the specimen image is a phase image. In other examples, the specimen image is a combined amplitude and phase image.

In some representative examples, the plurality of gratings includes, along an axis from the scannable X-ray source to the X-ray detector, a source grating, a phase grating, and an analyzer grating, and an X-ray fringe spatial frequency is based on an angle between an axis of the phase grating and an axis of the analyzer grating. In some alternatives, the scan controller is coupled to scan the scannable X-ray beam along an axis perpendicular to an axis of the source grating and the source grating and the analyzer grating are amplitude gratings. In typical examples, the analyzer grating is rotatable to establish a fringe frequency. In other examples, a fringe pattern is based on a geometric projection of a single or several absorption grids. The X-ray beam is scanned along an axis that does not coincide with lines of the fringe pattern.

Methods comprise situating a plurality of X-ray diffraction gratings or absorption grids so as to define an X-ray fringe generator. An X-ray beam is scanned with respect to the X-ray fringe generator so as to irradiate a specimen and form a plurality of fringe patterns modulated by the specimen. The fringe patterns are aligned and a specimen image is formed based on the aligned fringe patterns. In typical examples, the X-ray beam is scanned in a direction perpendicular to a set of fringe lines. In other examples, the X-ray beam is scanned in a direction between the axes of the lines of a two-dimensional fringe pattern. In typical examples, the plurality of gratings includes, along an axis from the scannable X-ray source to the X-ray detector, a source grating, a phase grating, and an analyzer grating. In some alternatives, a fringe frequency is established based on a relative orientation of the phase and analyzer gratings. In some examples, the source grating and the analyzer grating are amplitude gratings, and the analyzer grating is rotatable to establish a fringe frequency. In additional examples, a fringe frequency is established based on orientations of two of the plurality of gratings. In other examples, the fringe pattern is the geometric projection of absorption grids. The fringe frequency is determined by the frequency of the grid and a geometric magnification factor.

X-ray imaging apparatus comprise a fringe generator configured to establish a fringe pattern. A detector is situated to detect a plurality of specimen-modulations of the fringe patterns associated with X-ray irradiation of the specimen along a plurality of directions. An image processor is configured to associate each of a plurality of specimen locations with corresponding specimen-modulations of the fringe pattern and form a specimen image. In some alternative, the fringe pattern is fixed with respect to the direction of the X-ray irradiation. The fixed fringe pattern is defined by a first amplitude grating and a second amplitude grating. In additional examples, the first and second amplitude gratings are oriented so as to produce the fixed Moiré fringe pattern at a predetermined spatial frequency. In typical examples, the plurality of directions associated with the X-ray irradiation are along an axis perpendicular to a grating axis. In other examples, the fringe pattern is not fixed with respect to the direction of the X-ray irradiation, but movement of the fringe pattern is different from the movement of the projected profiles of the specimen when the X-ray beam source is scanned.

The foregoing and other objects, features, and advantages of the invention will become more apparent from the following detailed description, which proceeds with reference to the accompanying figures.

BRIEF DESCRIPTION OF THE DRAWINGS

FIG. 8D includes both measured and predicted data.

FIGS. 10A-10D are reconstructed images of a head region of a mouse, including differential phase contrast, phase contrast enhanced, dark field, and linear intensity attenuation images, respectively. Arrows in FIG. 10B indicate examples of features more visible in the phase contrast enhanced image than in the classic intensity attenuation image of FIG. 10D. The bright U-shaped object is a metallic ear tag.

FIGS. 11A-11D are reconstructed images of a torso region of a mouse, including differential phase contrast, phase contrast enhanced, dark field, and linear intensity attenuation images, respectively. Mouse lungs are most clearly visible in the image of FIG. 11C.

DETAILED DESCRIPTION

Figure 1:
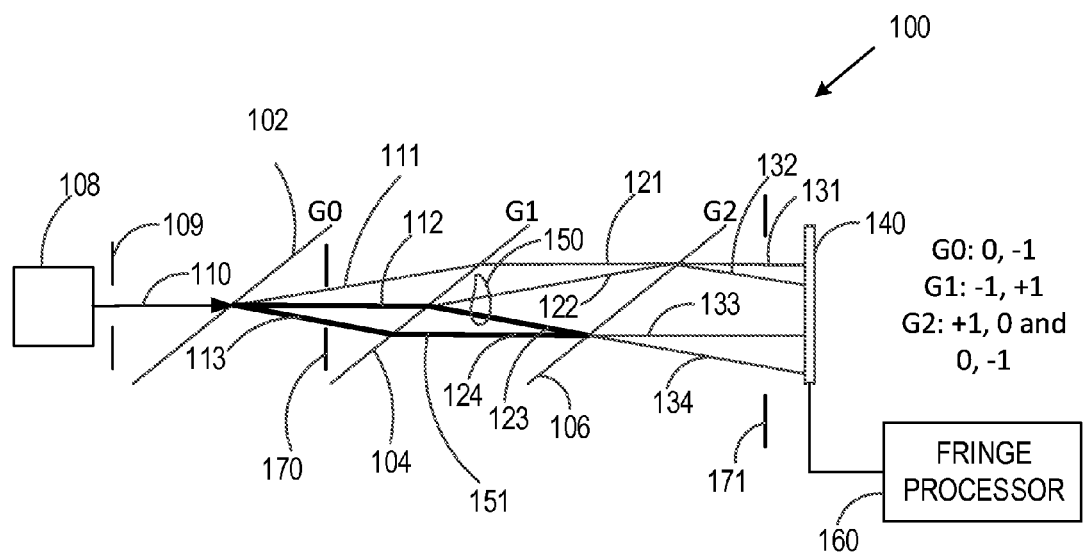
FIG. 1 is a schematic diagram of a representative X-ray fringe generator that includes a scanned X-ray beam source.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

Methods and apparatus are disclosed in which X-ray intensity patterns are demodulated to form images of a specimen. It is generally convenient to obtain a periodic intensity pattern using a coded aperture, a periodic absorber, a periodic scatterer, a periodic phase object, or other periodic phase/amplitude modulating aperture. Modulations at a fixed frequency are convenient, but more complex modulations can be used. As used herein, such phase/amplitude modulating devices are referred to as masks. Representative examples of such masks include phase or amplitude diffraction gratings, anti-scatter grids, or coded apertures. Such masks are generally periodic along a single direction or along two non-collinear axes. Masks can be multiply periodic along one or more axes. The disclosed methods and apparatus are applicable to X-ray imaging systems that produced an image with a periodic intensity modulation. More generally, X-ray beams having a modulation corresponding to such a mask can be referred to as providing structured irradiation, and the disclosed approaches permit demodulation of the imposed modulation. Systems that produce such modulations are referred to as fringe generators, wherein fringes refers to periodic (or almost periodic) intensity patterns that can be modulated based on specimen phase, scattering, or absorption properties.

The examples disclosed below pertain to X-ray interferometers using diffraction gratings. As used herein, X-rays refers to electromagnetic radiation at wavelengths between of 0.01 and 10 nm, frequencies between 30 PHz and 45 EHz, or energies between 100 eV and 150 keV. Diffraction gratings for such X-rays have grating periods between 10 nm and 1000 nm, 50 nm and 500 nm, or 100 nm and 250 nm. For examples, X-rays at a central energy of 22.5 keV and gratings having a grating period of 200 nm and a grating spacing along an axis of 65 cm can be used. This representative configuration produces a beam displacements of about 180 μm. Diffraction gratings include a distribution of phase and/or amplitude modulating features that is periodic along a grating axis. In typical examples, the modulating features are linear, parallel features, and the grating axis is perpendicular to these features and is aligned in a common direction throughout the grating. For gratings having non-linear features or non-parallel features, a grating axis can vary. Typical amplitude gratings have absorbing, attenuation, or reflective regions that alternate with more transmissive regions. Phase gratings have alternating regions of differing phase thickness. Gratings are frequently associated with a single spatial frequency or grating period, but gratings can have varying spatial frequencies and feature alignments.

As used herein, "image" refers to a viewable image of a specimen as well as stored representations of such viewable images. In some cases, image also refers to a detected, displayed, or stored fringe pattern.

X-Ray Grating Based Interferometers

For visible light, Mach-Zehnder interferometers permit achromatic, far field interferometry. Such interferometers define two interfering light paths that are balanced with each other, so that chromatic dispersion is eliminated. In X-ray optics, the Bonse-Hart interferometer is a type of Mach-Zehnder interferometer using X-ray Bragg diffraction in monolithic crystals to split and deflect X-ray beams. Momose et al. have used the Bonse-Hart interferometer to obtain absolute phase images. See Momose and Fukuda, "Phase-contrast radiographs of nonstained rat cerebellar specimen," Medical Physics 22:375-379 (1995). Imaging with Bonse-Hart interferometers requires narrow line width X-ray radiation due to the energy selectivity of Bragg diffraction in crystals. Thus, Bonse-Hart interferometers are unlikely to be useful in practical applications, and different approaches are needed.

More practical X-ray interferometers can be based on X-ray diffraction gratings. With reference to FIG. 1, a representative X-ray grating interferometer 100 includes X-ray gratings 102, 104, 106 arranged along an axis 110. As shown in FIG. 1, the gratings 102, 104, 106 are equally spaced along the axis 110, and spacings of at least as much as 100 cm can be used. An X-ray source 108 delivers an X-ray beam to the gratings 102, 104, 106 and diffracted X-ray beams are incident to a detector 140 that generates an electrical image signal associated with interference of at least some beams associated with selected X-ray diffraction orders. The X-ray beam is coupled through an aperture 109 that serves to block undesired X-ray radiation and/or to partially collimate the X-ray beam. The detector 140 is coupled to a fringe processor 160 that produces one or more images of a specimen 150 based on detected fringes. The gratings 102, 104, 106 are tilted with respect to the axis 110, but normal incidence can be used with suitable gratings. Slits 170, 171 can be situated to block any unwanted diffraction orders. Separations of diffraction orders are generally exaggerated in FIG. 1 for convenient illustration.

Each of the gratings can direct any input X-ray beam along a variety of paths corresponding to diffraction orders. These paths are at angles of $n\lambda/\Lambda$, wherein $\lambda$ is a wavelength associated with the input X-ray beam, n is an integer, and $\Lambda$ is a grating period. In the example of FIG. 1, the grating period is the same for gratings 102, 104, 106, and the gratings 102, 104 are phase gratings. In most examples, less X-ray power is diffracted into higher diffraction orders, i.e., those paths associated with larger values of n or −n. For convenience, upwardly directed diffraction orders shown in FIG. 1 are associated with n>0, and downwardly directed diffraction orders are associated with n<0. For example paths 111, 112, 113 correspond to +1, 0, and −1 diffraction orders of an X-ray beam input along the axis 110 to the grating 102. The 0 order propagating along path 112 is diffracted by the grating 104, and +1, −1 orders are shown as paths 122, 123, respectively. The −1 order propagating along path 113 is diffracted by the grating 104, and +1 order is shown as path 124. Other orders are not shown. At grating 106, a diffracted beam propagating along the path 123 is diffracted onto +1, 0 order paths 133, 134, respectively. A diffracted beam propagating along the path 124 is diffracted onto 0, −1 order paths which are the same as the paths 133, 134. Similarly diffracted beams are directed to the detector along paths 131, 132.

As shown in FIG. 1, the dual diffraction path 151 (shown with heavier lines) defined by paths 112, 113, 123, 124 provides substantially the same total phase delay for beams exiting along paths 133, 134 so that interference fringes are formed at the detector 140 even for X-ray beams with limited temporal coherence. Other paths also provide substantially equal phase delays and produce fringes as well, but are not indicated in FIG. 1. Typically, any paths between the gratings 102, 104 that form a parallelogram produce acceptable fringes. As used herein, paths that have substantially the same total phase delay are referred to as "balanced." Unbalanced paths can also be used to generate fringes, but can impose difficult coherence requirements on the input X-ray beam. The X-ray beam produced by the X-ray source 108 also exhibits lateral or transverse coherence, at least to some extent. Typically, a lateral coherence distance that is equal to or greater than about ¼ of the pitch of the grating 170 is satisfactory. Fringe contrast increases as coherence distance increases. Fringe visibility $V_M$ can be defined as $V_M = (I_{max} - I_{min})/(I_{max} + I_{min})$, wherein $I_{max}$ and $I_{min}$ are measured maximum and minimum fringe intensities. For lateral coherence distances of about 1 grating period or ¼ grating period fringe visibilities $V_M$ can be about 0.7 and 0.12, respectively. Thus, relatively low lateral coherence distances are satisfactory.

The specimen 150 is shown as situated between the gratings 104, 106 and interacting only along the path 123 and not the path 124. In other examples, the specimen is situated between gratings 102, 104 and is situated to intercept paths associated with both of interfering beams. If the specimen intercepts only one of the interfering paths, fringes are associated with absolute phase differences. If a specimen intercepts both interfering paths, fringes are associated with phase differences between different portions of the specimen. In one example, the gratings 102, 104, 106 have a common period of 200 nm and are spaced apart by 65 cm on the axis 110. One approach to image reconstruction is based on scanning or stepping at least one grating (such as the grating 104) to produce a plurality of fringe patterns that are acquired and processed to form phase based images. Alternatively, the X-ray beam can be scanned as discussed in detail below. Additional examples of grating based interferometers can be found in U.S. Provisional Patent Application 61/877,219, BALANCED TWO-ARM X-RAY GRATING INTERFEROMETER filed Sep. 12, 2013 and incorporated herein by reference. Other types of grating interferometers can also be used.

Figure 2:
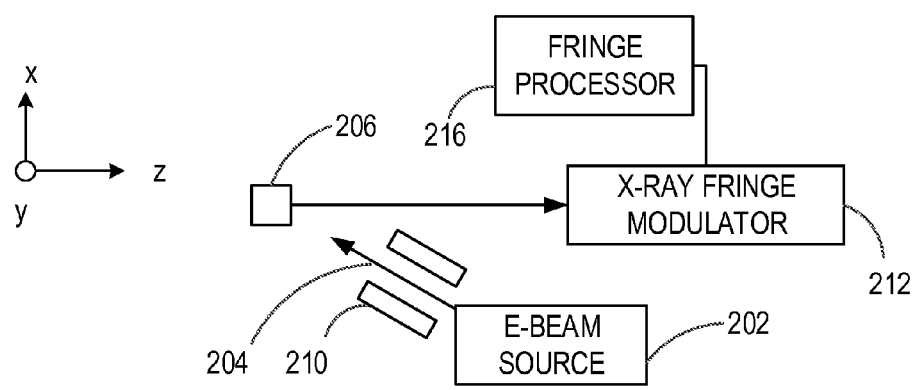
FIG. 2 is a block diagram of an X-ray fringe generator system that includes a scanned X-ray beam.

Scanning or stepping gratings can be inconvenient, and as disclosed herein, a location (real or virtual) of an X-ray source can be stepped or scanned to produce suitable fringe patterns, and scanning of interferometer components is unnecessary. An X-ray source can be stepped or scanned mechanically by, for example, a translation of an X-ray source along one or more axes, or along a curved or straight path. An X-ray source can also be scanned electromagnetically as illustrated schematically in FIG. 2. An electron beam source 202 is situated to deliver an electron beam along an axis 204 to an impact area on a target 206, and X-rays are generated at the impact area. An electron beam deflector 210 is configured to scan or step the electron beam at the target 206, thereby effectively scanning or stepping the X-ray beam. An X-ray interferometer 212 receives the scanned or stepped X-ray beam, and fringe patterns associated with the scanning or stepping are directed to a fringe processor 216 for image reconstruction. The electron beam deflector 210 can be an electrostatic, magnetic, or an electromagnetic deflector based on an applied electric field, an applied magnetic field, or a combination thereof. Typical deflectors can include coils (magnetic) and/or plates (electric), and beam deflection can be periodic or raster or vector scanned.

Figure 3:
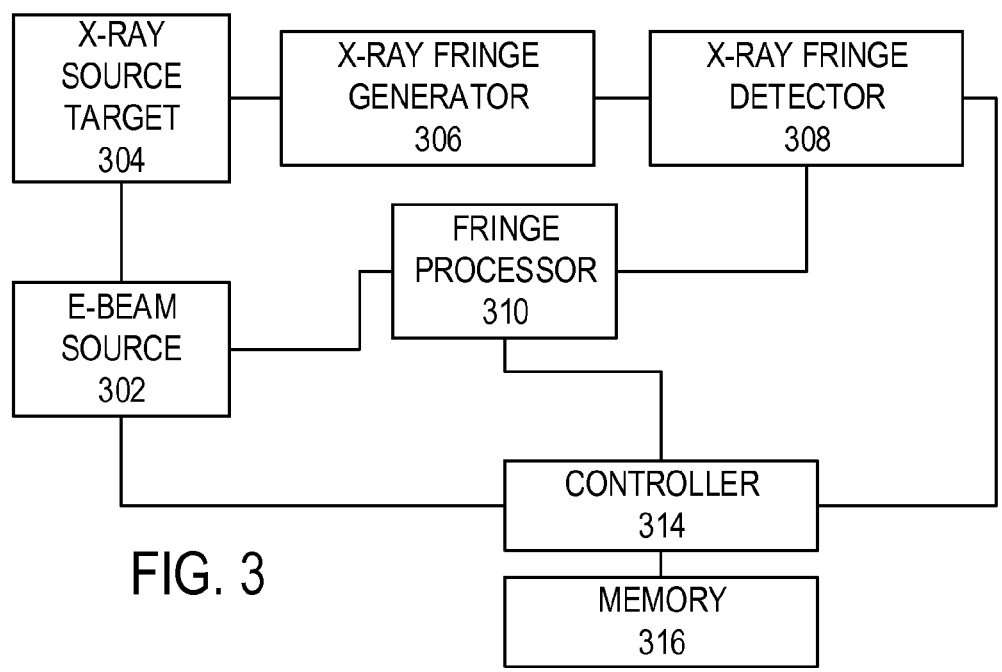
FIG. 3 is a block diagram of an X-ray fringe generator imaging system.

A representative X-ray grating based imaging system 300 is illustrated in FIG. 3. An electron beam source 302 is configured to produce an electron beam that is scanned with respect to an X-ray source target 304. The resulting X-ray beam is thus scanned and input to an X-ray interferometer 306 that is configured to produce fringe patterns associated with a specimen. A fringe detector 308 (typically an array detector) receives the fringe patterns and is coupled to a controller 314 so that fringe patterns are stored in a memory 316. The stored fringe patterns are coupled to a fringe processor 310 so that, based on X-ray beam displacement(s) and the stored fringe patterns, a specimen image is reconstructed. In some cases, the controller 314 is configured to process fringe patterns. The controller 314 can be coupled to a display or a network (not shown in FIG. 3), so that an image can be displayed or communicated to a remote location. In some examples, the fringe patterns and beam displacements are communication via a network for remote image reconstruction.

Figure 4:
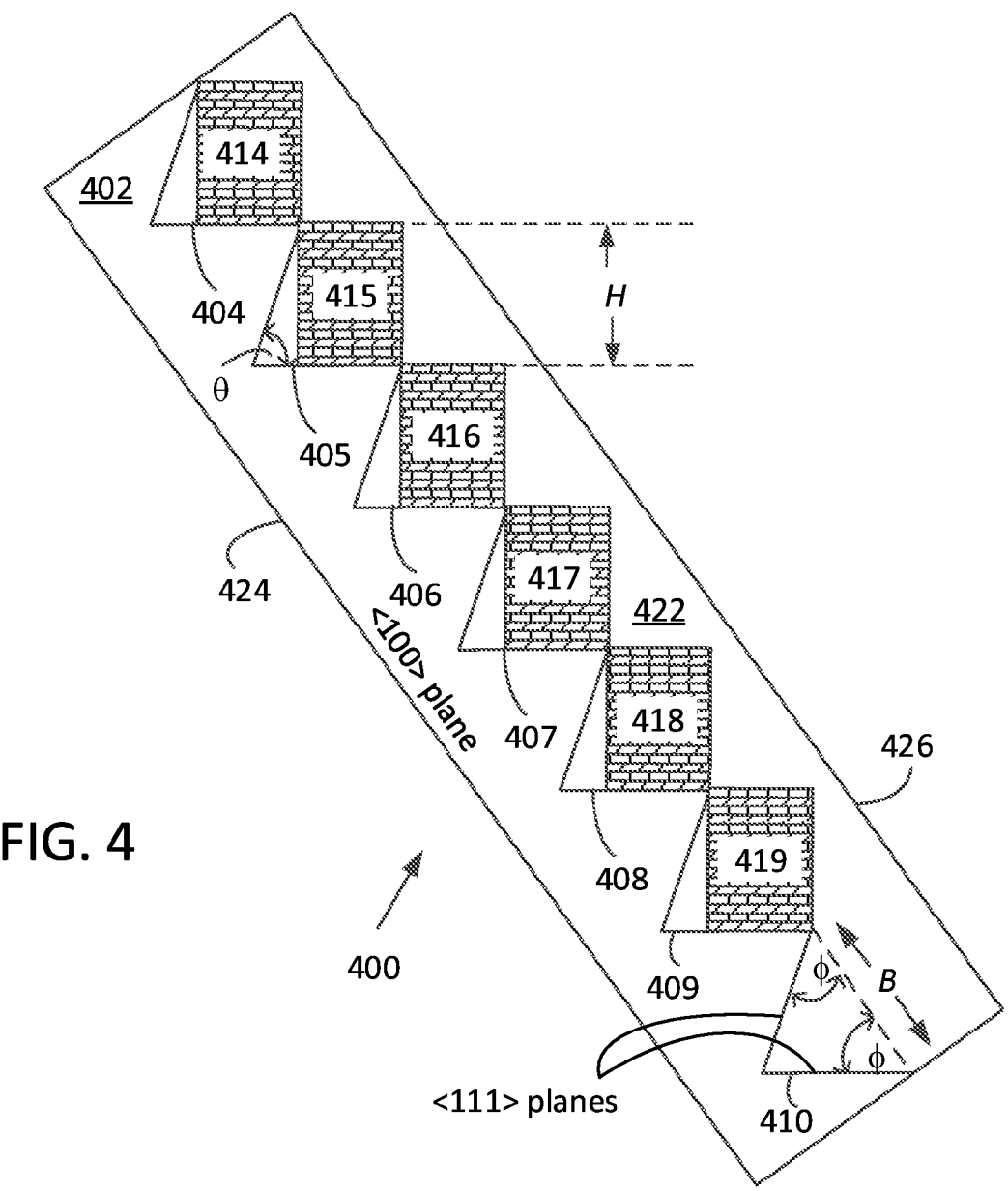
FIG. 4 illustrates a representative X-ray phase grating.

FIG. 4 illustrates a representative transmission X-ray grating 400. A stepped substrate 402 such as an anisotropically etched silicon substrate includes a plurality of steps 404-409 that are provided with respective multilayer coatings 414-419. For purposes of illustration, an uncoated step 410 is also shown in order to illustrate a grating tilt angle φ. In the etched silicon substrate 402, the steps 404-410 correspond to sides of isosceles triangles having a base of length B. The multilayer coatings 414-419 are preferably configured to have a height H that is substantially the same as the associated step height. The multilayer coatings 414-419 generally comprise a number of alternating bilayers of relatively less dense and relatively more dense materials. In the disclosed example, the etched silicon substrate 402 has a step height of about 8.16 μm, and the multilayer coatings 414-419 include 20 Si/W bilayers with each layer having a thickness of about 200 nm. A silicon filler layer 422 is provided over the etched silicon substrate 402 and the multilayer coatings 414-419. This layer can be formed by depositing a silicon layer followed by polishing. The X-ray grating 400 then has a uniform thickness with parallel exterior surfaces 424, 426. The combination of constant multilayer coating height matching the step height, and the silicon filler layer 422 eliminates or reduces grating substrate envelope modulation in interfering diffraction orders.

Transmission gratings such as that of FIG. 4 can exhibit diffraction with little or no envelope modulation due to the substrate if the bilayers are configured to have a height that is substantially the same as the step height H of the substrate steps and the filler layer 426 is provided. However, gratings with substrate modulation can be used as the substrate modulation is fixed and can be compensated in image analysis. In some examples, phase gratings are configured to provide greater intensities in diffraction orders that are to be used in fringe formation. For phase gratings, selection of a suitable phase or phases can be used. Some aspects of X-ray grating fabrication are found in Lynch et al., "Fabrication of 200 nm period centimeter area hard X-ray absorption gratings by multilayer deposition," J. Micromechanics and Microengineering 22:105007 (2012). Additional details of X-ray phase gratings can be found in Wen, "Multilayer-Coated Micro Grating Array for X-Ray Phase Sensitive and Scattering Sensitive Imaging," PCT Publication 2013/096974, which is incorporated herein by reference. Other types of X-ray gratings can also be used.

Figure 5:
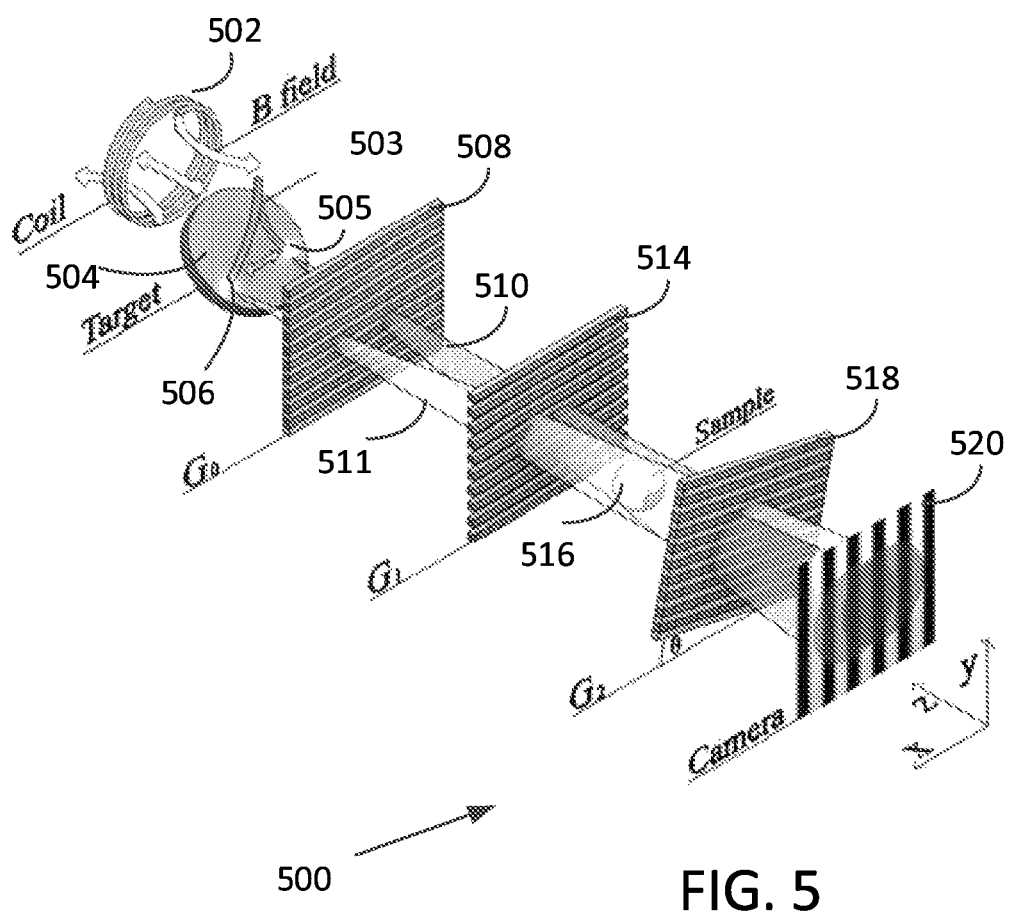
FIG. 5 is a perspective view of an electromagnetic fringe scanning apparatus based on a grating interferometer with a solenoid coil attached to an X-ray tube housing. A grating interferometer is an example of a fringe generator.

FIG. 5 is a perspective view of a representative X-ray imaging system 500 that can include an X-ray tube, a Talbot-Lau interferometer and an X-ray camera. Referring to FIG. 5, a coil 502 is configured to be energized so as to direct an electron beam 503 so as to strike a target 504 at varying locations such as locations 505, 506 that are separated along an x-axis. X-ray beams 510, 511 are directed (diffracted) by a source grating 508 to a phase grating 514. Each of the X-ray beams 510, 511 irradiates a sample 516 and then is incident to an analyzer grating 518 so that fringes 520 are formed at a detector plane 520. The coil 502 is configured to deflect the electron beam 503 so that target locations are displaced along an x-axis so that X-ray beams 510, 511 are similarly displaced along the x-axis. Displacement of the X-ray beam in a +x direction is associated with an image shift in the −x-direction; displacement of the X-ray beam in the −x direction is associated with an image shift in the +x-direction. In the example of FIG. 5, the gratings 508, 514 are situated so as provide a periodic X-ray phase or amplitude modulations in a y-direction and have periodic grating features that extend parallel to the x-axis. The analyzer grating 518 is situated so as to be rotatable about a z-axis so that features of the analyzer grating 518 are at an angle θ with respect to the features of the grating 514. The grating 518 can be secured so that the angle θ adjustable to provide fringes with an intended spatial frequency.

The interferometer of FIG. 5 includes amplitude gratings 508, 518 ($G_0$, $G_2$) and phase grating 514 ($G_1$). In one example implementation, a grating period is 4.8 μm. The amplitude grating 508 splits an X-ray cone beam into a number of thin line sources whose lateral coherent lengths are greater than the grating period at the plane of the grating 514 ($G_1$). Each line source creates an intensity fringe pattern, i.e., a fractional Talbot image of the grating 514 at the plane of the grating 518. Because the fringe period is usually smaller than a detector resolution, the grating 518 is configured to produce a broader Moiré pattern. When the distance between the gratings 508, 514 is the same as that between gratings 514, 518, the fringe pattern from each individual line source can sum constructively on the plane of the grating 518.

If the gratings 510, 514 are parallel and the grating 518 is rotated about an optical axis with respect to then grating 514 by the angle θ, sample differential phase information is encoded into Moiré fringes on the detector plane 520 as:

$$I \approx a_0 + a_1 \cos\left[\frac{2\pi}{p}\left(x\theta + \frac{\lambda d}{\pi}\frac{\partial \Phi}{\partial y}\right) + \phi_b\right],$$

wherein x and y are coordinates in the detector plane, $\alpha_0$ is an un-modulated baseline, $\alpha_1$ is a fringe amplitude, p is a grating period, d is a distance between the gratings, λ is an X-ray wavelength, and $\varphi_b$ is a background instrumental phase which depends on the positions of the gratings. The desired information is the derivative of the X-ray phase shift caused by the sample, expressed as $\partial \varphi / \partial y$ in the detector plane. In the example of FIG. 5, both diffracted X-ray beams are incident to the sample for differential phase measurements, but in other examples, only one of these beams interacts with the sample and absolute phase images can be formed.

Figure 6:
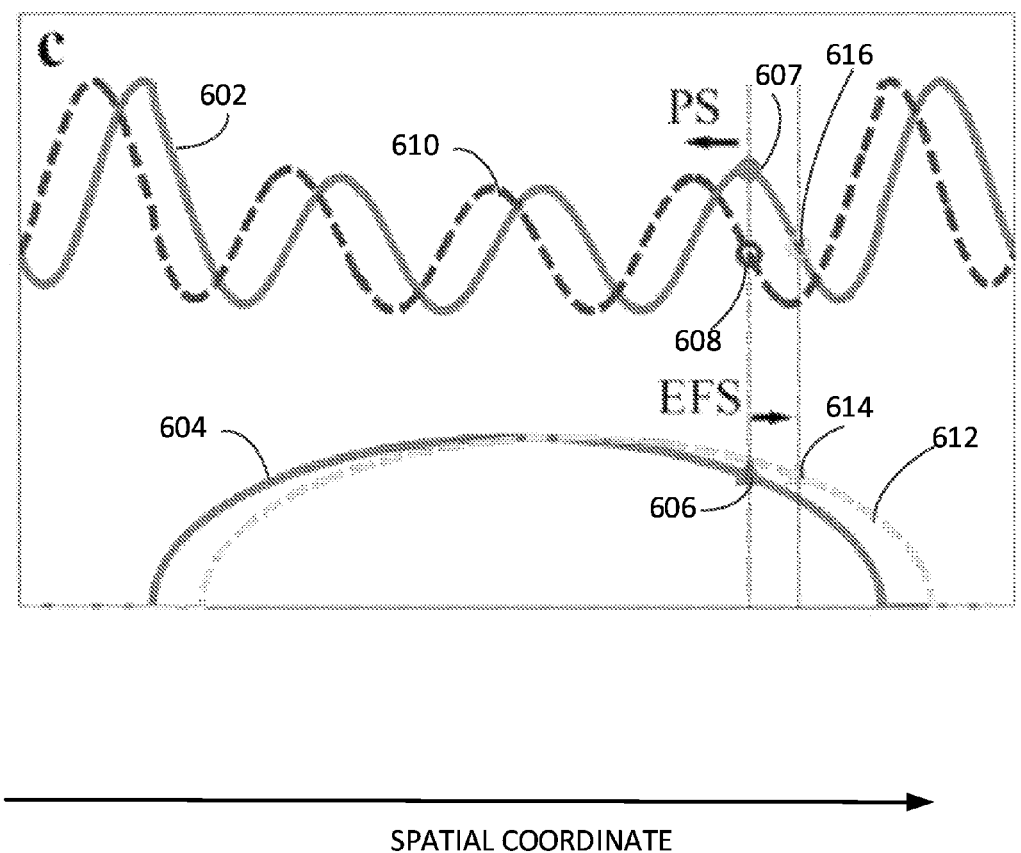
FIG. 6 illustrates electromagnetic fringe scanning (EFS) based on beam displacements in contrast with conventional phase stepping (PS) based on scanned gratings.

FIG. 6 is a schematic representation of fringes obtained by X-ray source scanning, referred to herein as electromagnetic fringe scanning (EFS). Curve 602 represents an interference or Moiré fringe pattern and curve 604 represents a projection of a sample under investigation at a selected scan position. Triangle 606 and dot 607 represent a specific location in the projection of the sample and its position in the fringe pattern, respectively. In conventional phase stepping (PS), moving one grating shifts the fringe pattern to a new position represented by the dashed curve 610. Consequently, the same location in the sample projection has a different fringe phase. For example, the fringe location indicated by the dot 607 changes as indicated by circle 608. In electromagnetic fringe scanning (EFS), the object projection is shifted (as represented by curve 612) by the displacement of the focal spot of the cone beam. This corresponds to moving the same location in the projection from the triangle 606 to triangle 614, with a corresponding shift on the fringe pattern (curve 602) from the dot 607 to circle 616. The fringe pattern represented by curve 604 does not move. Effectively, phase shifts are applied to specimen locations, but without shifts in the fringe pattern as in PS. Using this approach, a series of fringe patterns is recorded at incremental shifts of the X-ray beam focal spot. The fringe patterns of this series can be realigned so the fringe pattern appears to move as the X-ray beam is scanned.

Image Reconstruction Methods

A representative method of image reconstruction based on source shifted fringes is discussed below. The disclosed method is adaptive in two aspects: 1) owing to variable sample positioning and potential instrumental drifts, relative movement between a projection of the object and interference fringes in an electronic fringe scan is not known a priori, and can be determined retrospectively from the images themselves; and 2) once the projections are aligned, phase and amplitude images are retrieved from a set of arbitrary fringe positions, i.e., non-uniform and spatially varying phase intervals between successive images of a fringe scanned set of fringes can be used.

Figure 7:
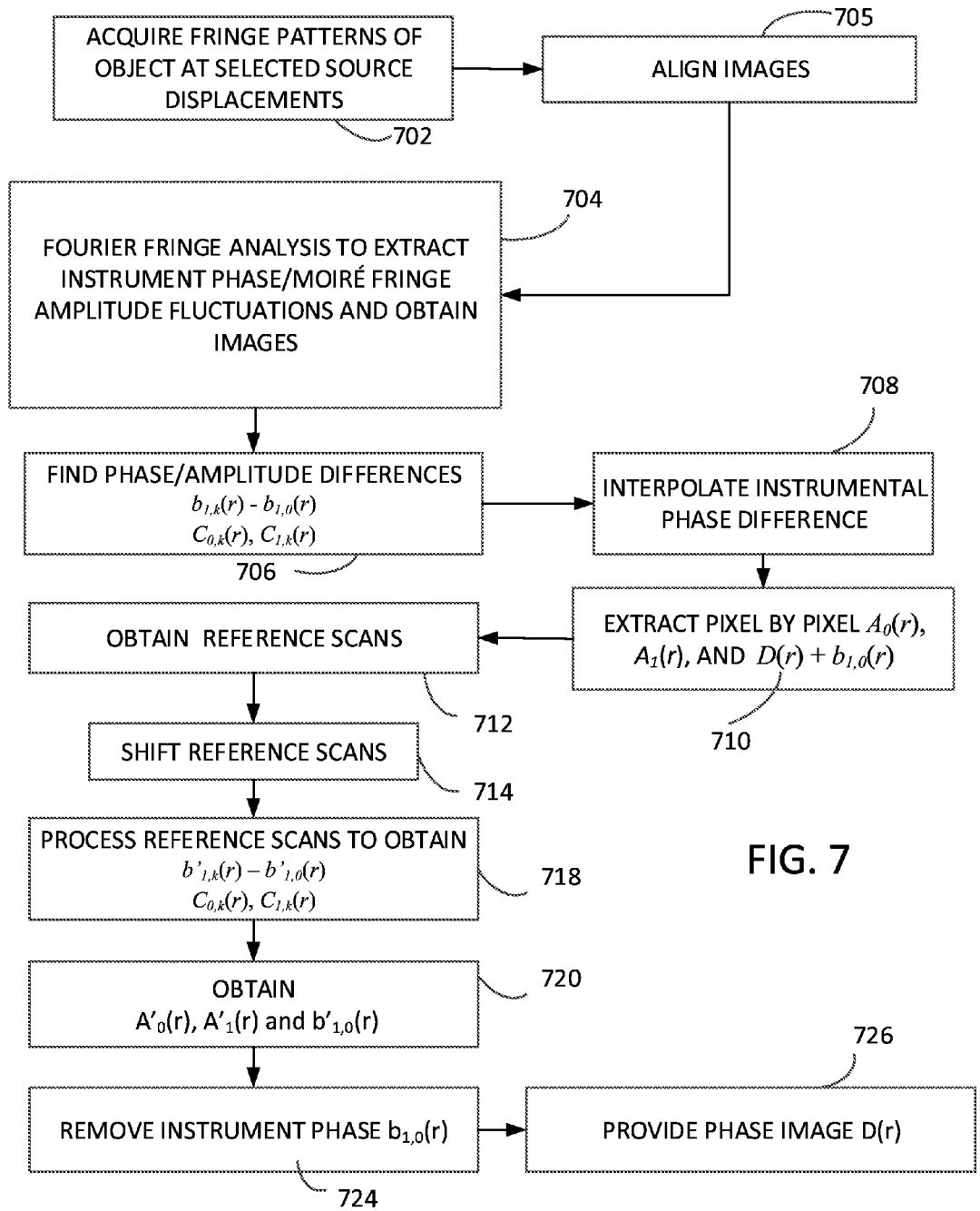
FIG. 7 is a block diagram of a representative method of image reconstruction based on X-ray diffraction patterns obtained at a plurality of X-ray beam positions.
Figure 8A:
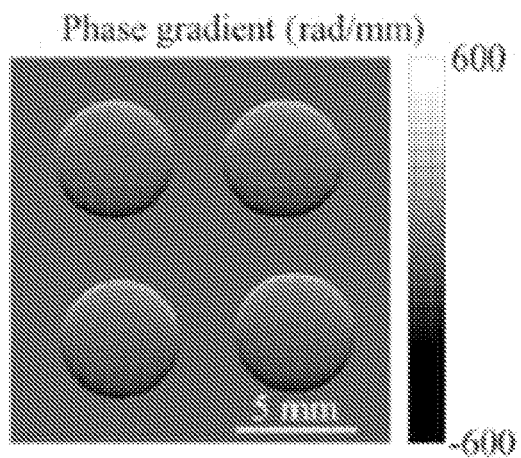
FIGS. 8A-8D illustrate processed linear intensity attenuation (FIG. 8A), differential phase contrast (DPC, shown in FIG. 8B), and phase shift (FIG. 8C) images of borosilicate spheres, obtained by direct integration of DPC information and baseline corrected through linear fitting, and a cross-sectional profile of phase shift through the center of a sphere (FIG. 8D), the location of which is marked by a line in the image of FIG. 8B.
Figure 8B:
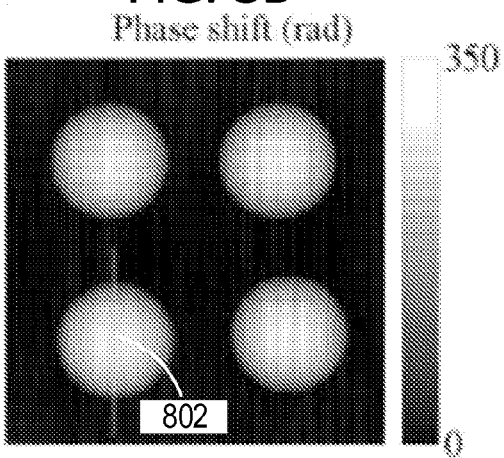
Figure 8C:
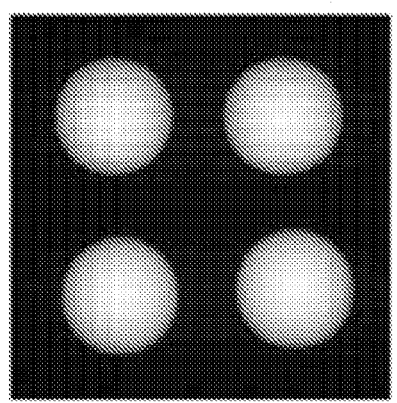
Figure 8D:
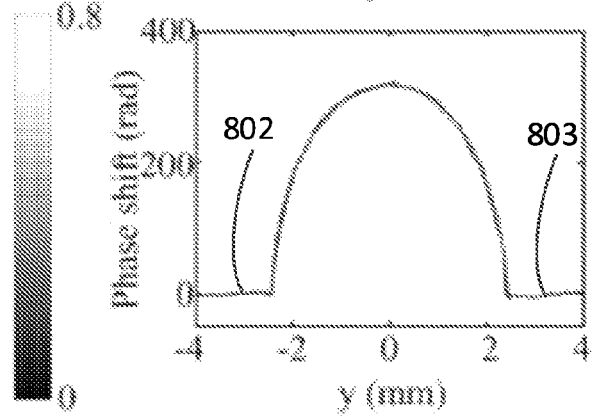

With reference to FIG. 7, at 702, a plurality of Moiré fringe patterns associated with corresponding X-ray beam displacements is acquired. Typically, a fringe scan is based on a plurality of electron beam deflections associated with an electrostatic, magnetic, or electromagnetic beam deflector. Each of the acquired Moiré fringe patterns is modulated in amplitude and in phase by a projection of a specimen. A small shift of the X-ray beam focal spot results in a displacement of the projection in an opposite direction, as well as a change of the projection angle. If the thickness of the specimen is small with respect to a distance between the X-ray beam source and a fringe detector, the movement of the projection is uniform throughout the sample, and the change in projection angle can be neglected. If the object is thick, then image reconstruction effectively focuses on a slice of the object in a way similar to tomosynthesis. The Moiré fringes may also move with the X-ray beam focal spot, although the movement is small when the source and phase gratings are arranged parallel to each other, as shown in FIG. 5.

At 705, the images are digitally shifted such that the projections of the sample are aligned among all images. The displacement of the source for a given electrical current input into the solenoid coil (502) is known from a calibration process. Then, for an image acquired with a source displacement of $d_s$, denoting the distance between the source and the focal plane and between the focal plane and the detector as $l_s$ and $l_d$, the image is digitally shifted in the direction of the source displacement by an amount $$\Delta = d_s \frac{l_d}{l_s}.$$

These shifts align the projections of any object that is positioned at the focal plane. The entire imaging process may be repeated for a series of focal planes to capture different sections of a thick object. After the images are aligned, the following steps are performed.

If the spatial frequency of the Moiré fringes in these fringe patterns is g, the aligned kth image of the electronic fringe scan can be expressed generally as:

$$I_k(r) = A_0(r)C_{0,k}(r) + \sum_{n>0} A_n(r)C_{n,k}(r)\cos\{n[2\pi gx + D(r)] + b_{n,k}(r)\},$$

wherein r represents two-dimensional coordinates in the image plane, x is a coordinate perpendicular to the Moiré fringes, n is a positive integer corresponding to a harmonic component centered around a spatial frequency ng, $A_0(r)$ is a smoothly varying part of the image intensity, i.e., lower frequency components, $A_n(r)$ are the amplitudes of the rapidly varying (i.e., higher frequency) components associated with the Moiré fringes, $D(r)$ is the differential phase signal from the object, and $b_{n,k}(r)$ represent phase shifts of the Moiré pattern in the kth image plus other instrument related phase contributions. $C_{n,k}(r)$ represent fluctuations of the mean intensity as well as the Moiré pattern amplitudes in the kth image. The phases bn,k(r) and amplitude fluctuations $C_{n,k}(r)$ are the quantities dependent on the fringe scan counter k.

For convenient illustration, a representative example of image reconstruction is described in which only the first harmonic (n=1) of the fringe images has a significant magnitude. The task of an image processing method is to obtain $A_0(r)$, $A_1(r)$ and D(r). These can be calculated from the set of fringe scanned images, if the instrument phase $b_{1,k}(r)$ and amplitude fluctuations $C_{0,k}(r)$, $C_{1,k}(r)$ are first extracted. These quantities can be obtained through a Fourier fringe analysis at 704 that demodulates the fringes by way of windowed filters in Fourier space. This procedure is described in, for example, Takeda et al., "Fourier-transform method of fringe-pattern analysis for computer-based topography and interferometry," JOSA 72:156 (1982), which is incorporated herein by reference. In this method, spatial variations of terms that do not involve the fringe frequency g are assumed to be at spatial frequencies much less than g. A Fourier transform of $I_k(r)$ is obtained, and segmented into a central band that is centered around the central zero spatial frequency, and side bands around harmonics of the fringe frequency at ±ng. The central band is inverse Fourier transformed to obtain an image of the mean intensity multiplied with the fluctuation factor, $A_0(r)C_{0,k}(r)$, at a reduced resolution which is approximately equal to the period of the Moiré fringes. The first sideband is transformed by shifting it back to the spatial frequency origin, and then inverse Fourier transformed. The phase of the result is obtained by estimating a complex logarithm of the inverse transform. The result is an amplitude image $A_1(r)C_{1,k}(r)$ and a phase image $D(r)+b_{1,k}(r)$ at a reduced resolution which is approximately equal to the period of the Moiré fringes.

At 706, a difference between the $k^{th}$ and the $0^{th}$ images is obtained to determine $C_{0,k}(r)$, $C_{1,k}(r)$ and $b_{1,k}(r)-b_{1,0}(r)$, again at the reduced resolution. If the periods of the gratings are uniform in space or are slowly varying, then the amplitude and phase differences $C_{0,k}(r)$, $C_{1,k}(r)$ and $b_{1,k}(r)-b_{1,0}(r)$ also varies smoothly in space. At 708, the low-resolution amplitude and phase differences can be interpolated in space to obtain $C_{0,k}(r)$, $C_{1,k}(r)$ and $b_{1,k}(r)-b_{1,0}(r)$ at a full resolution corresponding to detector pixel size. At 710, $A_0(r)$, $A_1(r)$ and the phase $D(r)+b_{1,0}(r)$ are obtained on a pixel-by-pixel basis by a least squares fitting procedure or other method.

At 710, the object phase D(r) and the instrumental phase $b_{1,0}(r)$ are obtained as a sum. The instrument contribution $b_{1,0}(r)$ can be removed from this phase map. However, it can be difficult to obtain instrument phase for parts of the object where X-rays are strongly scattered or attenuated, causing the Moiré fringes to become difficult to detect. At 712, a reference fringe scan set is obtained. The reference scans are obtained without the sample, typically using the same beam shifts as those used in obtaining the object scans. If desired, a reference object can be used that provides known phase contributions. At 714, the reference images are shifted by the same amount as determined in the alignment process of the sample scan as at 705. The instrumental amplitude and phase differences $C'_{0,k}(r)$, $C'_{1,k}(r)$ and $b'_{1,k}(r)-b'_{1,0}(r)$ are extracted at 718, and the amplitudes of $A'_0(r)$, $A'_1(r)$ and the instrumental phase $b'_{1,0}(r)$ are readily obtained at 720 (since D(r) is zero or other known value). In some cases, fringes are undetectable in some areas of the sample images, and the reference instrument amplitude and phase differences $C'_{0,k}(r)$, $C'_{1,k}(r)$ and $b'_{1,k}(r)-b'_{1,0}(r)$ can be used instead of the actual instrument phase difference $b_{1,k}(r)-b_{1,0}(r)$ with the object present, plus a correction that accounts for any instrumental drifts between acquisitions of the reference and object images. The correction is obtained by a linear fitting of the difference over areas where the Moiré fringes are well defined. The substitutions allow calculations of $A_0(r)$, $A_1(r)$ and $D(r)+b_{1,0}(r)$ across the full field of view.

At 724, the instrument phase $b_{1,0}(r)$ is removed based on, for example, substituting the reference instrument phase $b'_{1,0}(r)$ for $b_{1,0}(r)$, plus any correction associated with instrument drifts. Such correction can be obtained by linear fitting of the phase image $D(r)+b_{1,0}(r)-b'_{1,0}(r)$ over areas where the Moiré fringes do not vanish. The assumption for this correction is that the differential phase D(r) has minimal low spatial frequency content due to its differential nature. At 726, a differential phase image of the object D(r) is available.

A phase contrast image can be obtained as follow. If $A_0$ and φ are the linear attenuation and the phase shift of the X-ray wave front after propagation through the object, $A_0$ is simply the absolute value of the natural logarithm of the transmission, and $$\frac{\partial \Phi}{\partial y}$$

corresponds to the DPC signal. The derivative of the linear attenuation $$\frac{\partial A_0}{\partial y}$$

is incorporated into the DPC signal in a weighted sum of $$\frac{\partial A_c}{\partial y} = CW_0 \frac{\partial A_0}{\partial y} + W_1 \frac{\partial \Phi}{\partial y},$$

where C is a scaling factor between real and imaginary parts of refractive index, as disclosed by Roessl et al., "Image fusing algorithm for differential phase contrast imaging," Proc. of SPIE 8313: 831354. (2012), which is incorporated herein by reference. Weights $W_0$ and $W_1$ are determined locally according to the amplitude of the interference fringes $A_1$ and the noise level $N_1$ in the fringe amplitudes. Specifically, $W_0(r)=1/\{1+[A_1(r)/(2N_1)]^6\}$, and $W_1(r)=1-W_0(r)$. Once the combined differential image $$\frac{\partial A_c}{\partial y}$$

is determined, it is merged with the intensity attenuation data into a phase contrast enhanced image according to the algorithm described by Roessl (cited above): the direct integral of $$\frac{\partial A_c}{\partial y}$$

is high-pass filtered in Fourier space, and merged with a low spatial frequency part of linear intensity attenuation, then inverse Fourier transformed into a final image.

The absorption image of the object is simply the ratio of $A_0(r)/A'_0(r)$. The scattering or dark-field image measures additional attenuation of the interference fringes due to scattering in the object. It is given by $[A_1(r)/A'_1(r)]/[A_0(r)/A'_0(r)]$.

The above is based on the assumption that the thickness of the object is small relative to the distance between the source and the detector. Under this assumption, the small change of the projection angle associated with a shift of the source point has negligible effect. In the opposite situation where the object occupies a large portion of the distance between the source and the detector, the change of projection angle needs to be taken into account. The way to do so depends on the mode of imaging. In planar imaging, scanning the source point provides data similar to those of tomosynthesis. The above reconstruction algorithm for electromagnetic fringe scanning is based on translating the raw images by specific distances to align the object projection on the camera plane. This is valid for a slice at a specific distance from the source point. The result will have a depth-of-focus character, where the slice at the focal distance has the sharpest resolution. Features become blurred in front of and behind the focal plane. Other tomosynthesis reconstruction algorithms may also be used. In three-dimensional imaging by computed tomography, the imaging system is rotated around the object to cover a range of projection angles. In this case, the actual angle of the projection images should take into account the source point shifts. The corrected projection angles can then be used in the subsequent reconstruction steps.

Representative Implementation of an Imaging System

In one example, a tungsten-target X-ray tube operating at a peak voltage of 55 kV and a current of 1 mA was used as an X-ray source. The focal spot of the tube was approximately 50 μm. A Talbot-Lau interferometer consisting of three gratings of 4.8 μm period was used as shown in FIG. 5. The first and third gratings were intensity modulating (amplitude) gratings, the second was a phase grating. Grating lines were oriented horizontally. The amplitude gratings were defined by gold-filled trenches of 60 μm nominal depth in a polymer substrate and were rotated around the vertical axis (y-axis) by 45° to increase the effective gold height. The phase grating had un-filled trenches etched into a silicon substrate using the Bosch process as described in Wu et al., "High aspect ratio silicon etch:a review," J. Appl. Phys. 108:051101 (2010) which is incorporated herein by reference. The etch depth was 27 μm and the phase grating was also rotated by 45° to be parallel with the other gratings. The gratings were positioned at equal spacing over a total distance of 76 cm. The third grating was slightly rotated around the optical axis (z-axis) to create vertical Moiré intensity fringes of approximately 300 μm period. It should be noted that in such an arrangement of gratings, the Moiré fringes are largely independent of the position of the X-ray source. An X-ray camera having a pixel size of 30 μm and a 2048×2048 pixel matrix was used.

Electromagnetic fringe scanning was implemented with a copper solenoid coil of 60 mm inner diameter, having 200 turns attached to a front surface of an X-ray tube housing. The coil was driven by a digital power supply which provided up to 2.0 A of current at up to 8 W of power. Calculated peak magnetic field was 3.1 mT at the location of the electron beam inside the X-ray tube. The X-ray tube was situated so that the electron beam propagated vertically, along a y-direction. Under these conditions, the magnetic field shifted the focal spot by up to 380 μm (with 1.5 A current applied) in the horizontal direction, perpendicular to the Moiré fringes. The deflections of the focal spot at various levels of input current into the coil were measured experimentally. Six images were acquired in each fringe scan set based on corresponding scan positions.

As discussed above, three types of images can be obtained from a single set of raw images (fringe patterns): differential phase, linear attenuation and the dark field. In some applications, drift of the focal spot of the X-ray tube, drift in the alignment of the gratings and other components, and variable positioning of the imaged object may be compensated.

Images were reconstructed as discussed above, and representative examples are provided in FIGS. 8A-11D. FIGS. 8A-8D illustrate processed linear intensity attenuation (FIG. 8A), differential phase contrast (DPC, shown in FIG. 8B), and phase shift (FIG. 8C) images of borosilicate spheres, obtained by direct integration of DPC information and baseline corrected through linear fitting, and a cross-sectional profile of phase shift through the center of a sphere (FIG. 8D), the location of which is marked by a line 802 in the image of FIG. 8B.

Figure 9A:
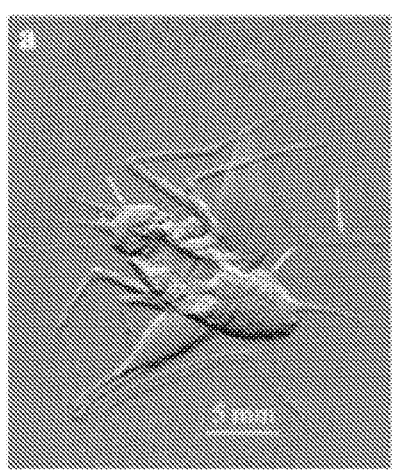
FIGS. 9A-9B are linear intensity attenuation and differential phase contrast images, respectively, of a cricket. A tungsten bead of 0.8 mm diameter is apparent in FIG. 9B near the head of the cricket as a marker and can be used to accurately determine the displacement of projection images during electromagnetic fringe scanning.
Figure 9B:
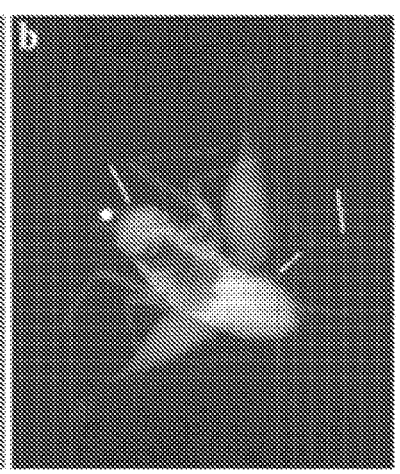

FIGS. 9A-9B are linear intensity attenuation and differential phase contrast images, respectively, of a cricket. A tungsten bead of 0.8 mm diameter is apparent in FIG. 9B near the head of the cricket as a marker and can be used to accurately determine the displacement of the projection images during electromagnetic fringe scanning.

FIGS. 10A-10D are reconstructed images of the head region a mouse, including differential phase contrast, phase contrast enhanced, dark field, and linear intensity attenuation images, respectively. Arrows in FIG. 10B indicate examples of features more visible in the phase contrast enhanced image than in the classic intensity attenuation image of FIG. 10D. The bright U-shaped object is a metallic ear tag.

FIGS. 11A-11D are reconstructed images of the torso region a mouse, including differential phase contrast, phase contrast enhanced, dark field, and linear intensity attenuation images, respectively. Mouse lungs are most clearly visible in the scattering image of FIG. 11C.

Figure 12:
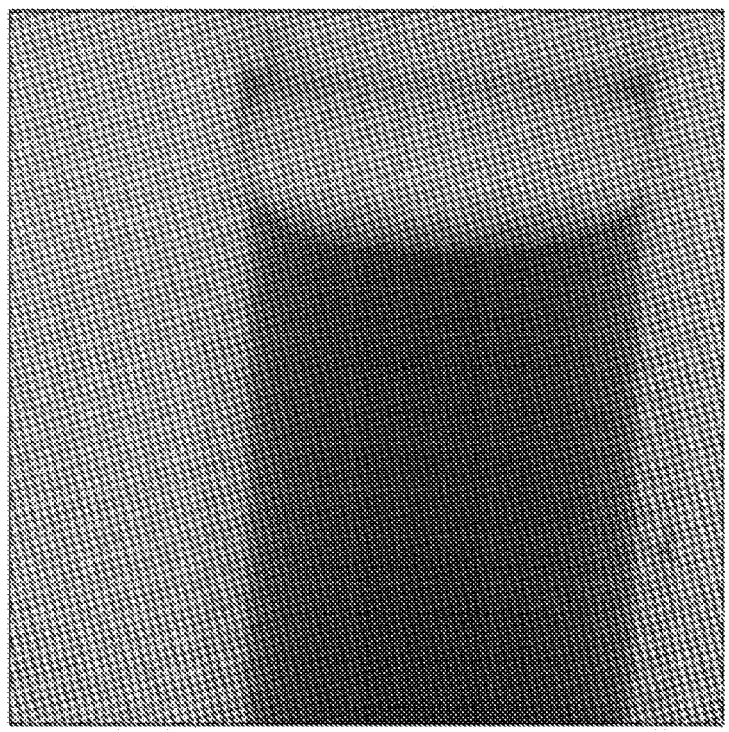
FIG. 12 is a raw image from a 2D absorption grid and a vial of perfluorocarbon micelle suspension in water.
Figure 13A:
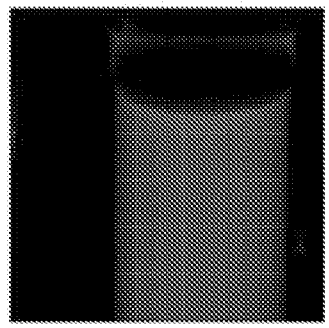
FIGS. 13A-13D include an attenuation image (FIG. 13C), and scattering (dark-field) images (FIGS. 13A-13B, 13D) in 3 directions from electromagnetic fringe scanning (phase stepping) in a single direction.
Figure 13B:
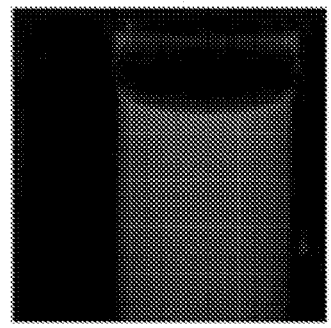
Figure 13C:
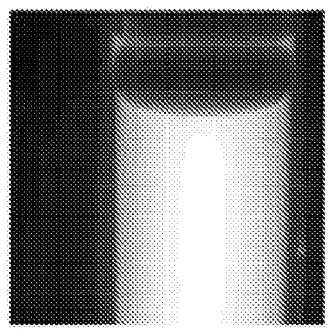
Figure 13D:
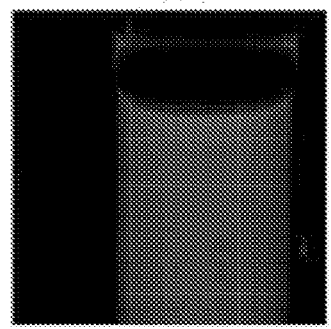

Grating-based X-ray imaging with two-dimensional gratings can provide scattering (dark field) and phase contrast images in multiple directions. Phase stepping in two directions can be used to demodulate a two-dimensional fringe pattern. In a 2D Fourier space, such images produce a 2D matrix of harmonic peaks. The task of phase stepping is essentially to separate these harmonic peaks. This can be accomplished by phase stepping in a single direction, and a minimum number of steps is equal to a number of harmonic peaks in the 2D Fourier space. This is done by rotating the gratings in-plane to the appropriate angle, such that the projections of the 2D harmonic peaks onto the axis of the phase stepping movement are evenly separated, with no two peaks having the same projection. Then, linear phase stepping causes different amounts of phase increments in the peaks, allowing them to be fully separated. FIG. 12 is a raw image from a 2D absorption grid and a vial of perfluorocarbon micelle suspension in water. FIG. 13C is an attenuation image, and FIGS. 13A-13B, 13D are scattering (dark-field) images in 3 directions produced with electromagnetic fringe scanning (phase stepping) in a single direction. In the arrangement of FIGS. 12-13D, a 2D square grid is used with a horizontal axis rotated to 13.8 degrees from the phase stepping axis.

Figure 14:
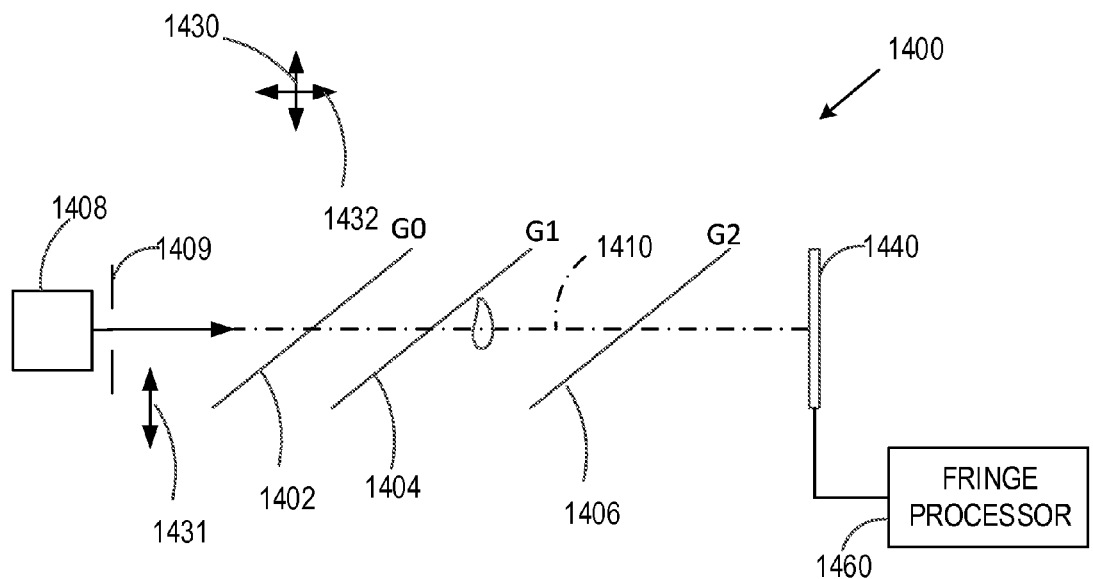
FIG. 14 illustrates a representative X-ray fringe generator that includes a scanned X-ray beam source and at least one grating that can be scanned or stepped along a beam axis of propagation.

While particular scanning configurations are described above, a variety of fringe and beam shifts can be used to produce X-ray images. With reference to FIG. 14, a representative X-ray grating interferometer 1400 includes X-ray gratings 1402, 1404, 1406 arranged along an axis 1410. An X-ray source 1408 delivers an X-ray beam to the gratings 1402, 1404, 1406 and diffracted X-ray beams are incident to a detector 1440 that generates an electrical image signal associated with interference of at least some beams associated with selected X-ray diffraction orders. The X-ray beam can be coupled through an aperture 1409 that serves to block undesired X-ray radiation and/or to partially collimate the X-ray beam. In some cases, such an aperture is unnecessary, and the detector can receive multiple diffraction orders. The detector 1440 is coupled to a fringe processor 1460 that produces one or more images of a specimen (not shown) based on detected fringes. The gratings 1402, 1404, 1406 are tilted with respect to the axis 1410, but normal incidence can be used with suitable gratings. Slits can be situated to block any unwanted diffraction orders, but in some cases, slits are unnecessary. Diffraction orders are not shown in FIG. 14 for convenient illustration, but are described above.

Grating adjustments in a system such as that of FIG. 14 can be used to obtain or vary Moiré fringes. For example, one (or more) of the gratings 1402, 1404, 1406 can be shifted in a direction 1430 that is perpendicular to the axis 1410 and to grating lines associated with the gratings 1402, 1404, 1406. Depending on a magnitude and direction in which a grating is shifted, Moiré fringes can be more or less dense. A beam from the source 1408 can be similarly shifted as shown at 1431 so as to move the beam across the grating lines. Acquisition of associated fringe patterns permits an image of an object to be obtained.

In other examples, one or more gratings can be moved along the axis 1410 in a direction 1432. Depending on a direction of motion, fringes can become less dense or more dense. A beam from the source 1408 can be shifted in the direction 1431 so as to move the beam across the grating lines and acquisition of associated fringe patterns permits an image of an object to be obtained. In some cases, such translations can be preferred as fewer image artifacts are produced. For example some commercially available X-ray gratings have cross-bridge supporting structures that prevent the gratings from collapsing. Such structures can introduce image artifacts. Selection of a direction of grating displacement can reduce or eliminate such artifacts as a particular direction may be available that exhibit reduced artifacts. In other examples, one (or more) of the gratings 1402, 1404, 1406 can be rotated about the axis 1410.

Combinations of two dimensional linear translations and rotation of one or more gratings can be used. Slight rotations of a grating (typically, a few arc minutes) can produce fringes that are perpendicular to grating lines. Increasing rotation angles are associated with denser fringes. Shifting gratings produces horizontal fringes (i.e., fringes that are parallel to grating lines); shift distance can be varied to select fringe density. By combining grating rotation and grating translation (shift along an axis or perpendicular to grating lines), oblique fringes can be produced at an angle and with a density set by rotation angle and total shift. With a particular fringe configuration, a source beam can be scanned or stepped with respect to the fringes, either parallel or perpendicular to the fringes (or at some other angle with respect to the fringes). In some cases, scanning/stepping an X-ray beam in a direction perpendicular to the fringes results in image artifacts due to grating structure; scanning or stepping in a direction parallel to the fringes tends to produce images without artifacts or with reduced artifacts. In some X-ray apparatus, source scanning/stepping is limited to only certain directions; combining grating rotations and displacements permits fringes to be suitably aligned with respect to preferred or possible beam scanning/stepping directions. In this way, Moiré fringes can be "tuned" as needed based on source scanning/stepping limitations.

Image processing based on Fourier transform is described above. In some examples, fringe data is Fourier transformed, masked or otherwise filtered, and then inverse transformed. In other examples, wavelet transforms (referred to herein as space-frequency transforms) are used. A wavelet transform of image data produces a function of frequency and image position. A suitable wavelet can be selected producing spatial frequency variation that can correspond to fringe density variation. For example, if fringes are less dense (i.e., lower spatial frequency) on a right hand image side and more dense (higher spatial frequency on a left hand side, a variable wavelet transform can be used having a corresponding frequency variation. Wavelet width can be varied so that a number of pixels processed varies within an image data set.

A wavelet generally correlates with image data when the wavelet and the image data are associated with a similar frequency or frequencies. Thus, matching a wavelet transform permits identification of image frequency (i.e., fringe frequency). Fringe shift is used to establish phase images, and such shifts can be determined from the fringe frequency associated with a wavelet. Some variations in fringe frequency correspond to grating variations (such as in warped gratings), and these variations can be identified and accommodated with a wavelet transform. Using wavelet transforms, fringe shifts from image to image can be accurately obtained even in the presence of significant amplitude variations.

As discussed above, source scanning/stepping and fringe formation are arranged in various ways to produce relative motion between fringes and projections of the object under investigation in order to produce images. Typically, an X-ray beam can be scanned or stepped only so far. Moving a grating along an axis in a first direction produces fringe motion in the same direction as that of the scanned/stepped projection of an object. Moving the grating along the axis in a second, opposite direction, produces fringe motion in a direction opposite to that of the scanned/stepped projection direction. Typically, relative motions of fringes and object projections that are greater than a period of the fringes permit superior images to be produced.

Having described and illustrated the principles of the disclosed technology with reference to the illustrated embodiments, it will be recognized that the illustrated embodiments can be modified in arrangement and detail without departing from such principles. For instance, elements of the illustrated embodiments shown in software may be implemented in hardware and vice-versa. Also, the technologies from any example can be combined with the technologies described in any one or more of the other examples. It will be appreciated that procedures and functions such as those described with reference to the illustrated examples can be implemented in a single hardware or software module, or separate modules can be provided. The particular arrangements above are provided for convenient illustration, and other arrangements can be used.

We claim:
1. An apparatus, comprising:
an X-ray source configured to produce a scannable X-ray beam;
at least one periodic mask situated to receive the scannable X-ray beam, direct at least a portion of the scannable X-ray beam to a specimen, and produce X-ray fringes modulated by the specimen;

a scan controller coupled to scan the scannable X-ray beam to a plurality of positions and produce a corresponding plurality of X-ray fringe patterns;

an X-ray detector situated to receive the X-ray fringe patterns and produce associated electronic images; and an image processor configured to align the electronic images associated with the X-ray fringe patterns and produce a specimen image based on the aligned electronic images.

2. The apparatus of claim 1, wherein the X-ray source includes an electron beam source that is directed to a target so as to produce the scannable X-ray beam, and a coil coupled to scan the scannable X-ray beam based on a current applied to the coil.

3. The apparatus of claim 1, wherein the image processor is configured to produce the specimen image based on the aligned electronic images of the specimen and aligned electronic images associated with a set of reference X-ray fringe patterns.

4. The apparatus of claim 3, wherein the specimen image is a phase image.

5. The apparatus of claim 1, wherein the specimen image is an amplitude image.

6. The apparatus of claim 1, wherein the specimen image is a combined amplitude and phase image.

7. The apparatus of claim 1, wherein the at least one periodic mask includes a plurality of diffraction gratings.

8. The apparatus of claim 7, wherein at least one of the diffraction gratings is a phase grating.

9. The apparatus of claim 1, wherein the at least one periodic mask is an anti-scatter grid.

10. The apparatus of claim 1, wherein at least one mask comprises a plurality of gratings that includes, along an axis from the scannable X-ray source to the X-ray detector, a source grating, a phase grating, and an analyzer grating, and an X-ray fringe spatial frequency is based on an angle between an axis of the phase grating and an axis of the analyzer grating.

11. The apparatus of claim 10, wherein the scan controller is coupled to scan the scannable X-ray beam in a direction parallel to lines of the source grating.

12. The apparatus of claim 11, wherein the source grating and the analyzer grating are amplitude gratings.

13. The apparatus of claim 10, wherein the analyzer grating is rotatable to establish a fringe frequency.

14. The apparatus of claim 1, wherein the at least one mask is a scattering or absorbing mask defined by a one or two dimensionally periodic array of absorbing or scattering features.

15. A method, comprising:

situating at least one X-ray masks as to define an X-ray fringe generator;

scanning an X-ray beam with respect to the X-ray fringe generator so as to irradiate a specimen and form a plurality of fringe patterns modulated by the specimen; and aligning the fringe patterns and forming a specimen image based on the aligned fringe patterns.

16. The method of claim 15, wherein the at least one mask includes a plurality of diffraction gratings situated to form the X-ray fringe generator.

17. The method of claim 16, wherein the X-ray beam is scanned in a direction perpendicular to an axis of at least one of the plurality of X-ray gratings.

18. The method of claim 17, further comprising establishing a fringe frequency based on a relative orientation of the source and analyzer gratings.

19. The method of claim 18, wherein the source grating and the analyzer grating are amplitude gratings, and the analyzer grating is rotatable to establish a fringe frequency.

20. The method of claim 17, further comprising establishing a fringe frequency based on orientations of two of the plurality of gratings.

21. The method of claim 16 wherein the plurality of gratings includes, along an axis from the scannable X-ray source to the X-ray detector, a source grating, a phase grating, and an analyzer grating.

22. The method of claim 15, wherein the at least one mask includes a periodic absorbing or scattering mask.

23. The method of claim 22, wherein the periodic absorbing or scattering mask is a two dimensional grid.

24. The method of claim 23, wherein the two dimensional grid is periodic with respect to first and second axes, and the X-ray beam is scanned along an axis other than the first and second axes.

25. The method of claim 15, wherein a relative displacement of the fringe patterns among the plurality of images is determined by a wavelet transform of the fringe patterns.

26. An X-ray imaging apparatus, comprising:

a grating interferometer configured to establish a fixed Moiré fringe pattern;

a detector situated to detect a plurality of specimen-modulations of the fixed Moiré fringe patterns associated with X-ray irradiation of the specimen along a plurality of directions; and an image processor configured to associate each of a plurality of specimen locations with corresponding specimen-modulations of the fixed Moiré fringe pattern and form a specimen image.

27. The X-ray imaging apparatus of claim 26, wherein the Moiré pattern is defined by a first amplitude grating and a second amplitude grating.

28. The X-ray imaging apparatus of claim 26, wherein the first and second amplitude gratings are oriented so as to produce the fixed Moiré fringe pattern at a predetermined spatial frequency.

* * * * *